(12) United States Patent
Willis et al.

(10) Patent No.: US 6,514,887 B1
(45) Date of Patent: Feb. 4, 2003

(54) FLUORINATED TRIAZINE MONOMERS

(75) Inventors: Colin R Willis, Salisbury (GB); Stuart A Brewer, Salisbury (GB); Brian G Jones, Salisbury (GB)

(73) Assignee: The Secretary of State for Defence, Hampshire (GB)

( * ) Notice: Subject to any disclaimer, the term of this patent is extended or adjusted under 35 U.S.C. 154(b) by 0 days.

(21) Appl. No.: 09/463,497

(22) PCT Filed: Jul. 16, 1998

(86) PCT No.: PCT/GB98/02104

§ 371 (c)(1),
(2), (4) Date: Apr. 6, 2000

(87) PCT Pub. No.: WO99/05127

PCT Pub. Date: Feb. 4, 1999

(30) Foreign Application Priority Data

Jul. 26, 1997 (GB) ............................................. 9715709

(51) Int. Cl.⁷ .......................... B32B 27/04; B32B 27/12; C08F 126/06
(52) U.S. Cl. .............................. 442/82; 442/79; 442/80; 526/261
(58) Field of Search .............................. 442/79, 80, 82; 526/201

(56) References Cited

U.S. PATENT DOCUMENTS 4,476,215 A * 10/1984 Kausch ...................... 430/281
5,629,066 A * 5/1997 Yonemura et al. ......... 428/64.3

FOREIGN PATENT DOCUMENTS

| EP | 1102903 | * | 2/1968 | |
| EP | 0 366 884 A | | 5/1990 | |
| EP | 366884 | * | 9/1990 | ......... C07D/251/54 |
| EP | 519420 A1 | * | 12/1992 | ............... C08J/7/04 |
| EP | WO 97/13024 | * | 4/1997 | .......... D06M/14/00 |
| GB | 1 102 903 | | 2/1968 | |
| JP | 6-82601 | * | 6/1994 | ............ G02B/1/04 |
| WO | WO 97 13024 A | | 4/1997 | |

* cited by examiner

*Primary Examiner*—Cheryl A. Juska
*Assistant Examiner*—Christopher C. Pratt
(74) *Attorney, Agent, or Firm*—Nixon & Vanderhye P.C.

(57) ABSTRACT

A compound of formula (I), wherein $R^1$ and $R^2$ are independently selected from saturated fluorocarbon substituted side chains, such as $NR^5(CH_2)_nC_mF_{2m+1}$, $O(CH_2)_nC_mF_{2m+1}$, $S(CH_2)_nC_mF_{2m+1}$, $NR^5S(O)_2(CH_2)_pC_mF_{2m+1}$, or $CR^5[CO_2(CH_2)_nC_mF_{2m+1}]_2$, where $R^5$ is hydrogen or alkyl, n and m are independently an integer of 1–12, and p is 0 or an integer of 1–12, $R^3$ is an unsaturate moiety which may be polymerised, and X is O, S or $NR^4$ where $R^4$ is hydrogen or alkyl, as well as methods for the preparation of these compounds. Compounds of formula (I) are useful monomers in the preparation of oil- and water-repellent polymers.

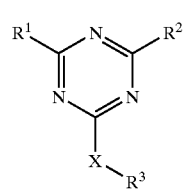

(I)

15 Claims, No Drawings

FLUORINATED TRIAZINE MONOMERS

The present invention relates to novel monomeric compounds which can be used in the production of polymers which have a high degree of oil and water-repellency and which may be fixed to substrates such as clothing, to processes for their preparation and to polymers produced therefrom.

Oil- and water-repellent treatments are in widespread use, in particular for outdoor clothing applications, sportswear, leisurewear and in military applications. These treatments generally require the incorporation of a fluoropolymer into or more particularly, fixed onto the surface of the clothing fabric. The degree of oil and water repellency is a function of the number of fluorocarbon groups or moieties that can be fitted into the available space. The greater the concentration of such moieties, the greater the repellency of the finish.

In addition however, the polymeric compounds must be able to form durable bonds with the substrate. Oil- and water-repellent textile treatments are generally based on fluoropolymers that are applied to fabric in the form of an aqueous emulsion. The fabric remains breathable and permeable to air since the treatment simply coats the fibres with a very thin, liquid-repellent film. In order to make these finishes durable, they are sometimes co-applied with cross-linking resins that bind the fluoropolymer treatment to fibres. Whilst good levels of durability towards laundering and dry-cleaning can be achieved in this way, the cross-linking resins can seriously damage cellulosic fibres and reduce the mechanical strength of the material. WO 97/13024 discloses a group of fibre reactive polymers, which include a functional group such as a triazine group, which binds the polymer to the material substrate.

British patent No 1,102,903 describes certain fluoro alkyl containing compounds which are used in water- and oil-repellent compositions.

The applicants have produced certain novel monomers, which give rise to polymers which have a high number of fluorocarbon substituents per monomer unit.

The present invention provides a compound of formula (I)

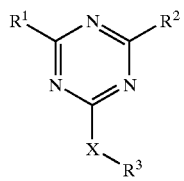

(I)

wherein $R^1$ and $R^2$ are independently selected from saturated fluorocarbon substituted side chains;

$R^3$ is an unsaturated moiety which may be polymerised, and X is O, S or $NR^4$ where $R^4$ is hydrogen or alkyl.

As used herein, the term "alkyl" refers to straight or branched chain alkyl or cycloalkyl groups, in particular those having from 1 to 12 and preferably from 1 to 6 carbon atoms. The term "saturated" refers to groups which do not contain carbon-carbon double bonds. Conversely the term "unsaturated" refers to groups which include carbon-carbon double bonds.

Suitable fluorocarbon substituted side chains for $R^1$ and/or $R^2$ include groups which are hydrophobic groups which are able to confer water- and/or oil- repellency on the resultant polymer. In particular $R^1$ and $R^2$ are independently selected from $NR^5(CH_2)_nC_mF_{2m+1}$, $O(CH_2)_nC_mF_{2m+1}$, $S(CH_2)_nC_mF_{2m+1}$, $NR^5S(O)_2(CH_2)_pC_mF_{2m+1}$ or $CR^5[CO_2(CH_2)_nC_mF_{2m+1}]_2$, where $R^5$ is hydrogen or alkyl, and n and m are independently an integer of 1–12, and p is 0 or an integer of from 1–12.

Conveniently $R^1$ and $R^2$ are the same. They are preferably selected from $O(CH_2)_nC_mF_{2m+1}$ or $NR^5S(O)_2(CH_2)_pC_mF_{2m+1}$. Suitably $R^5$ is methyl, ethyl or n-propyl, in particular ethyl. Preferred integers for n and p are from 1–3, suitably 2, whilst preferred integers for m are from 6 to 10, most preferably 8.

Suitable polymerisable groups $R^3$ are alkenes or alkynes which may also include a functional group such as an acyloxy group. Particularly preferred groups for $R^3$ are groups of formula $(CH_2)_qOC(O)C(R^6)CR^7R^8$ where q is an integer of from 1 to 12, suitably from 1 to 4 and especially 2, and $R^6$, $R^7$ and $R^8$ are independently selected from hydrogen or alkyl such as $C_{1-4}$ alkyl. Preferably $R^6$, $R^7$ and $R^8$ are all hydrogen.

Compounds of formula (I) are suitably prepared by reacting a compound of formula (II)

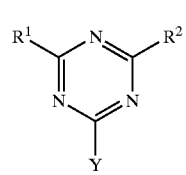

(II)

where $R^1$ and $R^2$ are as defined in relation to formula (I) and Y is a leaving group, with a group of formula (III)

$$R^a-X-R^{3'}$$ (III)

where X is as defined in relation to formula (I) and $R^3$ is a group $R^3$ as defined in relation to formula (I) or a precursor group which may be reacted to form a group $R^3$ and $R^8$ is hydrogen or alkyl; and thereafter if necessary converting a precursor group $R^3$ to a group $R^3$.

Preferably $R^a$ is hydrogen or a lower alkyl, for example a $C_{1-3}$ alkyl, in particular methyl.

Suitable leaving groups for Y include halogen such as fluorine and chlorine, in particular chlorine, or amine leaving groups such as substituted pyridines for instance nicotinic acid or colladine.

The reaction is suitably effected in an organic solvent such as tetrahydrofuran (THF), acetone, toluene or chloroform. It may be effected at temperatures of from 0 to 200° C., suitably from 25 to 150° C., depending upon the precise nature of the reactants and solvents involved. Conveniently the reaction may be effected at room temperature or under reflux conditions.

Preferably the reaction is effected under basic conditions. Weak bases may suffice, and in some instances, the compound of formula (III) may itself act as an acid scavenger and so the use of an excess, particularly a 2 molar excess of the compound of formula (III) will ensure that that the reaction proceeds effectively.

Suitable groups $R^{3'}$ which are precursor groups to $R^3$ would be apparent to the skilled person. For example, where $R^3$ is a group $(CH_2)_qOC(O)C(R^6)CR^7R^8$, a suitable precursor group $R^3$ would be $(CH_2)_qOH$, which can be readily converted to $R^3$ by reaction with a suitable acid halide for example an acid chloride of formula $ClC(O)C(R^6)CR_7R^7$ in the presence of a base, such as a weak base, for example pyridine or a pyridine derivative such as collidine. This reaction is suitably effected in an organic solvent such as toluene at elevated temperatures, conveniently at the reflux temperature of the solvent.

Certain compounds of formula (II) are known (see for example British Patent No. 1,102,903). These compounds can be prepared by reacting a compound of formula (IV)

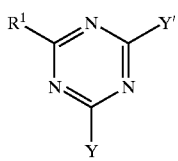

(IV)

where $R^1$ is as defined in relation to formula (I), Y is as defined in relation to formula (II) and Y' is a leaving group, with a compound of formula (V)

$R^2H$ (V)

where $R^2$ is as defined in relation to formula (I), in the presence of a base.

Suitable bases are those which react with a compound of formula (V) so as to produce a nucleophilic moiety of formula (V')

$(R^2)^-$ (V')

Thus the selection of suitable bases will depend upon the precise nature of the group $R^2$ and will be readily understood or determinable by the skilled person. For example, where $R^2$ is a group $O(CH_2)_nC_mF_{2m+1}$, strong bases such as alkali metal hydroxides, in particular lithium hydroxide, may be used. Alternatively, where $R^2$ is a group $NR^5S(O)_2(CH_2)_p C_mF_{2m+1}$, stronger bases such as alkali metal alkoxides, in particular sodium or potassium methoxide or ethoxide may be used.

Compounds of formula (IV) are suitably prepared by reacting a compound of formula (VI)

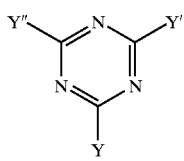

(VI)

wherein Y, Y' and Y" are the same or different leaving groups, with a compound of formula (VII)

$R^1H$ (VII)

where $R^1$ is as defined in relation to formula (I), in the presence of a base.

Reaction conditions will be generally similar to those described above in relation to the reaction between compounds of formula (IV) and formula (V).

Where compounds of formula (V) and formula (VII) are the same, compounds of formula (II) may be prepared directly in one pot. If necessary, the reaction can be controlled in a stepwise manner in order to maximise yield of the target compound by controlling the reaction temperature. For example, where $R^1$ and $R^2$ are groups of formula $NR^5S(O)_2(CH_2)_nC_mF_{2m+1}$, the compound of formula (IV) may be prepared at depressed temperatures, for example at about −78° C. Allowing the reaction mixture to warm up to approximately 0° C. will produce a compound of formula (II) after suitable work-up.

Compounds of formula (III), (V), (VI) and (VII) are either known compounds or they can be prepared from known compounds using conventional methods. A preferred compound of formula (VI) is cyanuric chloride.

Compounds of formula (I) may be polymerised or copolymerised using conventional technology, e.g emulsion polymerisation.

Polymers or copolymers including units of formula (VIII)

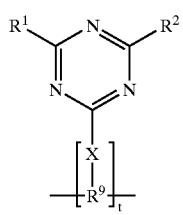

(VIII)

where $R^1$, $R^2$ and X are as defined in relation to formula (I), t is an integer in excess of 5, and $R^9$ is a saturated derivative of $R^3$ as defined in relation to formula (I) form a preferred embodiment of the invention.

In particular $XR^9$ will be a moiety of formula (IX)

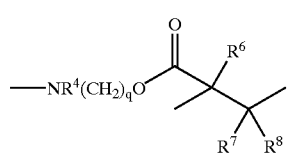

(IX)

Suitably the monomers of the invention are copolymerised with a monomer which comprises a fibre reactive moiety for example as described in WO 97/13024.

The invention will now be particularly described by way of example.

EXAMPLE 1

Step 1

Synthesis of 2-chloro-4,6-bis(N-Ethylperfluorooctylsulphonamido)-1,3,5-triazine

Metallic sodium (4.08 g, 177 mmols) was reacted with methanol (150 mls). N-Ethyl perfluorooctyl sulphonamide (93.28 g, 177 mmols) was added, and the resulting solution was stirred for 30 minutes. The methanol was removed at the pump (a vacuum pump was required to remove the final traces of solvent). The resulting sticky solid was dissolved in acetone (300 mls) and cooled to −65° C. under argon. Recrystalised cyanuric chloride (16.33 g, 88.5 mmols) dissolved in acetone (100 mls) was added to the reaction mixture dropwise such that the temperature did not rise above −50° C. (~1 hour). After the addition, the reaction mixture was allowed to slowly warm to room temperature (1 hour) and then stirred for a further 3 hours. The precipated solid was removed by filtration and dried under vacuum. Purification by soxhlet extraction with acetone afforded 61 g (56.9%) of a fine white powder.

$^1$H NMR (CDCl$_3$) δ (ppm) 4.20 (2H, q, $^3J_{H-H}$ 6.8 Hz, C$\underline{H}_2$CH$_3$), 1.40 (3H, t, $^3J_{H-H}$ 6.8 Hz, CH$_2$C$\underline{H}_3$) $^{13}$C{$^1$H} NMR (CDCl$_3$) δ (ppm) 171.3, 165.0 (triazine), 46.3 (C$\underline{H}_2$CH$_3$), 14.5 (CH$_2$C$\underline{H}_3$).

Step 2

Synthesis of 2-N-{4,6-bis(N-ethylperfluorooctylsulphonamido)-1,3,5-triazin-2-yl}-amino Ethanol A THF solution (85 mls) of 2-chloro-4,6-bis(N-ethylperfluorooctylsulphonamido)-1,3,5-triazine (15 g, 12.9 mmols) and ethanolamine (1.6 g, 26.2 mmols) were heated under reflux for 1 hour. The hot solution/suspension was filtered and the product was allowed to crystalise overnight to afford 12.8 g (83%) of product.

$^1$H NMR ($d_6$acetone) δ (ppm) 4.85 (4H, m, N$\underline{CH_2}$CH$_3$), 4.38 (2H, t, $^3J_{H-H}$ 5 Hz, CH$_2$O), 4.22 (2H, dt, 5, 5 Hz, OCH$_2$ $\underline{CH_2}$N), 2.05 (6H, m NCH$_2\underline{CH_3}$).

Step 3

Synthesis of 2-N-{(4,6-bis(N-Ethylperfluorooctylsulphonamido)-1,3,5-triazin-2-yl)}-aminoethyl Propenoate 2-N-[4,6-bis(N-ethylperfluorooctylsulphonamido)-1,3,5-triazin-2-yl]amino ethanol (11.58, 9.7 mmols) and acryloyl chloride (1.32 g, 14.6 mmols) were dissolved in hot toluene (80 mls). Collidine (1.77 g, 14.6 mmols) was added as a toluene solution (10 mls) down the reflux condenser. The resulting reaction mixture was heated under reflux for 2 hours and then filtered hot. Toluene was removed at the pump and the resulting solid dissolved in diethyl ether (400 mls). The etheral solution was washed with 1M HCl (2×50 mls) distilled water (2×40 mls) and then dried over sodium sulphate. Filtration and evaporation of the solvent at the pump afforded 8.8 g (73%) of product.

$^1$H NMR (CDCl$_3$) δ (ppm) 6.42 (1H, dd, $^3J_{H-H}$ 17.3, 1.3 Hz, CH=$\underline{CH_2}$ $_{trans}$), 6–11 (1H, dd, 3$J_{H-H}$ 17.3, 10.5 Hz, $\underline{CH}$=CH$_2$), 5.88 (2H, m, NH, CH=$\underline{CH_2}$ $_{cis}$), 4.32 (2H, t, $^3J_{H-H}$ 5.3 Hz, CH$_2$O), 4.13 (4H, m, N$\underline{CH_2}$CH$_3$), 3.72 (2H, m, OCH$_2\underline{CH_2}$N), 1.36 (6H, m, NCH$_2\underline{CH_3}$).

$^{13}$C{$^1$H} NMR (CDCl$_3$) δ (ppm) 166.0, 165.6, 164.6, 164.3, (triazine/C=O), 131.5 (C=C), 127.8 (C=C), 62.5 ($\underline{CH_2}$O), 45.4 (CH$_3\underline{CH_2}$N), 40.5 ($\underline{CH_2}$N), 14.9 ($\underline{CH_3}$CH$_2$).

EXAMPLE 2

Synthesis of 2-[N-Methyl-N-{(4,6-bis(N-ethylperfluorooctylsulphonamido)-1,3,5-triazin-2-yl)}]-aminoethyl Propenoate 2-Chloro-4,6-bis(N-ethylperfluorooctylsulphonamido-)1,3,5-triazine (20 g, 17.2 mmols) was held as a solution/suspension in chloroform (150 mls). N,N-Dimethylethylamino acrylate (2.459, 17.2 mmols) was added dropwise, over a period of 30 minutes, as a chloroform solution (50 mls). The reaction mixture was stirred for 3 hours at room temperature. The chloroform solution was filtered through Celite®, concentrated (to a volume of approximately 30 mls) and then passed through a short path column of silica. Product was eluted with chloroform. Evaporation of the solvent afforded 19 g (88%) of a sticky oil that crystalised with time (2 days).

$^1$H NMR (CDCl$_3$) δ (ppm) 6.37 (1H, dd, $^3J_{H-H}$ 17.3, 1.5 Hz, CH=$\underline{CH_2}$ $_{trans}$), 6.09 (1H, dd, $^3J_{H-H}$ 17.3, 10.5 Hz, $\underline{CH}$=CH$_2$), 5.83 (1H, dd, $^3J_{H-H}$ 10.5, 1.5 Hz, CH=$\underline{CH_2}$ $_{cis}$), 4.36 (2H, t, $^3J_{H-H}$ 5.6 Hz, CH$_2$O), 4.14 (4H, m, N$\underline{CH_2}$CH$_3$), 3.86 (2H, t, $^3J_{H-H}$ 5.6 Hz, OCH$_2\underline{CH_2}$N), 3.20 (3H, S, CH$_3$N), 1.38 (6H, m, NCH$_2\underline{CH_3}$). $^{13}$C{$^1$H} NMR (CDCl$_3$) δ (ppm) 165.8, 164.5, 164.2, 164.0, (triazine/C=O), 131.3 (C=C), 127.9 (C=C), 61.7 ($\underline{CH_2}$O), 48.3 ($\underline{CH_2}$N), 45.5 ($\underline{CH_2}$N), 36.3 (CH$_3$N), 15.0 ($\underline{CH_3}$CH$_2$).

EXAMPLE 3

Step 1

Synthesis of 2,4-bis(1H,1H,2H,2H-Perfluorootoxy)-6-chloro-1,3,5-triazine

Lithium hydroxide (0.49 g, 11.7 mmols) and 1H, 1H, 2H, 2H perfluorooctanol (5.4 g 11.7 mmols) were held as a solution/suspension in tetrahydrofuran (25 mls). Cyanuric chloride (1.08 g, 5.8 mmols) and distilled water (1 ml) were added and the reaction mixture was stirred at room temperature overnight. The resulting solution/suspension was precipitated into distilled water (200 mls) and extracted with diethyl ether (2×200 mls). The organic extract was dried over sodium sulphate, filtered and the diethyl ether was removed at the pump. The resulting white solid was recrystalised form diethyl ether (50 mls), to afford 3.3 g (54%) of product.

$^1$H NMR (CDCl$_3$) δ (ppm) 4.75 (2H, t, $^3J_{H-H}$ 6.6 Hz, O$\underline{CH_2}$CH$_2$), 2.63 (2H, tt, $^3J_{H-F}$ 18.1 Hz, $^3J_{H-H}$ 6.6 Hz OCH$_2$ $\underline{CH_2}$). $^{13}$C{$^1$H} NMR (CDCl$_3$) δ (ppm) 173.2, 171.7 (triazine), 61.1 (O$\underline{CH_2}$CH$_2$), 30.5 (t, $^2J_{C-F}$ 22.0 Hz OCH$_2$ $\underline{CH_2}$CF$_2$).

Step 2

Synthesis of 2-[N-methyl-N-{(4,6-bis(1H,1H,2H,2H-perfluorooctoxy-)1,3,5-triazin-2-yl)}]-aminoethyl Propenoate 2,4-bis(1H,1H,2H,2H-perfluorooctoxy)-6-chloro-1,3,5-triazine (0.5 g, 0.48 mmols) was held as a solution/suspension in chloroform (10 mls). N,N-Dimethylethylamino acrylate (0.076 g, 0.53 mmols) was added dropwise as a neat liquid at room temperature and the reaction mixture was stirred for 2 hours. The chloroform solution was extracted with 2M HCl (2×10 mls), distilled water (2×10 mls), dried over sodium sulphate and filtered. Evaporation of the solvent afforded 0.48 g (90%) of product as a waxy solid.

$^1$H NMR (CDCl$_3$) δ (ppm) 6.30 (1H, d, $^3J_{H-H}$ 17.2 Hz, CH=CH$_2$ $_{trans}$), 6.00 (1H, dd, $^3J_{H-H}$ 17.3, 10.4 Hz, $\underline{CH}$=CH$_2$), 5.75 (1H, d, $^3J_{H-H}$ 10.4 HZ, CH=$\underline{CH_2}$ $_{cis}$), 4.57 (4H, m, CF$_2$CH$_2\underline{CH_2}$O), 4.31 (2H, t, 5.5 Hz, O$\underline{CH_2}$CH$_2$N), 3.84 (2H, t, $^3J_{H-H}$ 5.5 Hz, OCH$_2\underline{CH_2}$N), 3.14 (3H, s, CH$_3$N), 2.56 (4H, m, CF$_2\underline{CH_2}$CH$_2$O). $^{13}$C{$^1$H} NMR (CDCl$_3$) δ (ppm) 171.3, 171.1, 167.3, 165.8, (triazine/C=O), 131.1 (C=C), 128.0 (C=C), 61.8 ($\underline{CH_2}$O), 59.2 ($\underline{CH_2}$N), 48.0 ($\underline{CH_2}$N), 36.1 (CH$_3$N), 30.2 (t, 22 Hz, $\underline{CH_2}$CF$_2$).

What is claimed is:

1. A compound of formula (I)

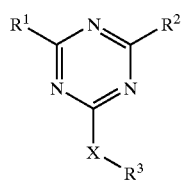

(I)

wherein $R^1$ and $R^2$ are independently selected from $NR^5$ $(CH_2)_nC_mF_{2m+1}$, $O(CH_2)_nC_mF_{2m+1}$, $S(CH_2)_nC_mF_{2m+1}$, $NR^5S(O)_2(CH_2)_pC_mF_{2m+1}$ or $CR^5[CO_2(CH_2)_nC_mF_{2m-1}]_2$, where $R^5$ is hydrogen or $C_1$–$C_3$ alkyl, n and m are independently an integer of 1–12, and p is 0 or an integer of from 1–12; $R^3$ is an unsaturated moiety which may be polymerized, and X is O, S or $NR^4$ where $R^4$ is hydrogen or $C_1$–$C_{12}$ straight or branched chain alkyl or cycloalkyl.

2. A compound according to claim 1 wherein $R^1$ and $R^2$ are the same.

3. A compound according to claim 1 wherein $R^1$ and $R^2$ are selected from $O(CH_2)_nC_mF_{2m+1}$ or $NR^5S(O)_2(CH_2)_pC_mF_{2m+1}$.

4. A compound according to claim 1 wherein $R^3$ is a group of formula $-(CH_2)_qOC(O)CR^6=CR^7R^8$ where q is an integer of from 1 to 12, and $R^6$, $R^7$ and $R^8$ are independently selected from hydrogen or a $C_{1-4}$ alkyl.

5. A compound according to claim 4 where $R^6$, $R^7$ and $R^8$ are all hydrogen.

6. A method of preparing a compound of formula (I) as defined in claim 1, which method comprises reacting a compound of formula (II)

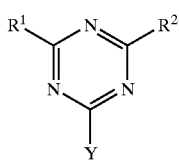

(II)

where $R^1$ and $R^2$ are as defined in claim 1 and Y is a leaving group, with a group of formula (III)

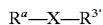

(III)

where X is as defined in claim 1 and $R^{3'}$ is a group $R^3$ as defined in relation to formula (I) or a precursor group which may be reacted to form a group $R^3$ and $R^a$ is hydrogen or a $C_{1-3}$ alkyl group; and thereafter if necessary converting a group $R^{3'}$ to a group $R^3$.

7. A method according to claim 6 wherein $R^{3'}$ is a group of the formula $(CH_2)_qOH$, and this is subsequently converted to $R^3$ by reaction with an acid halide of formula $ZC(O)C(R^6)=CR^7R^8$ where Z is a halogen and $R^6$, $R^7$ and $R^8$ are as defined in claim 5, in the presence of a base.

8. A method according to claim 6 wherein the compound of formula (II) is prepared by reacting a compound of formula (IV)

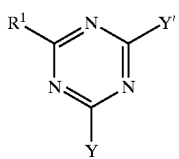

(IV)

where $R^1$ is as defined in relation to formula (I), Y is as defined in relation to formula (II) and Y' is a leaving group, with a compound of formula (V)

(V)

where $R^2$ is as defined in relation to formula (I), in the presence of a base.

9. A method according to claim 8 wherein the compound of formula (IV) is prepared by reacting a compound of formula (VI)

(VI)

wherein Y, Y' and Y" are the same or different leaving groups, with a compound of formula (VII)

(VII)

where $R^1$ is as defined in claim 1, in the presence of a base.

10. A method according to claim 9 wherein the compound of formula (IV) is converted to a compound of formula (II) in situ.

11. A polymeric compound which has been derived from a compound of formula (I) of claim 1.

12. A polymeric compound according to claim 11 which comprises a polymer or copolymer including repeating units of formula (VIII)

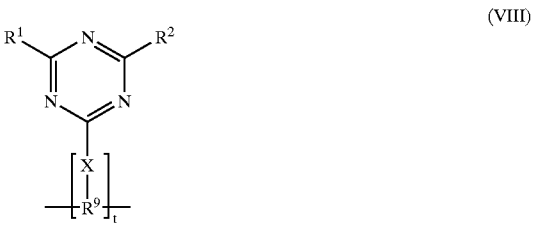

(VIII)

where $R^1$, $R^2$ and X are define in relation to formula (I), t is an integer in excess of 5, and $R^9$ is a saturated derivative of $R^3$ as defined in relation to formula (I).

13. A polymeric compound according to claim 12 wherein $XR^N$ is a moiety of formula (IX)

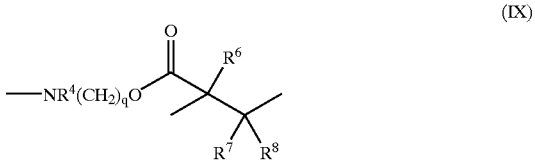

(IX)

where q, $R^6$, $R^7$ and $R^8$ are as defined in claim 4.

14. A substrate which is coated with a polymeric compound according to claim 11.

15. A substrate according to claim 14 which is a fabric.

* * * * *